(12) United States Patent
Harding et al.

(10) Patent No.: US 12,246,145 B2
(45) Date of Patent: Mar. 11, 2025

(54) DRESSING-BASED TRACTION DEVICE AND RELATED SYSTEMS AND METHODS

(71) Applicant: Becton, Dickinson and Company, Franklin Lakes, NJ (US)

(72) Inventors: Weston F. Harding, Lehi, UT (US); Megan Scherich, Salt Lake City, UT (US); Jonathan Karl Burkholz, Salt Lake City, UT (US); Yiping Ma, Layton, UT (US); John Lackey, West Valley City, UT (US); Tyler Warner, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 83 days.

(21) Appl. No.: 17/339,555

(22) Filed: Jun. 4, 2021

(65) Prior Publication Data

US 2021/0402151 A1    Dec. 30, 2021

Related U.S. Application Data

(60) Provisional application No. 63/045,700, filed on Jun. 29, 2020.

(51) Int. Cl.
*A61M 25/02* (2006.01)
*A61F 13/00* (2024.01)
*A61F 13/02* (2024.01)

(52) U.S. Cl.
CPC ............. *A61M 25/02* (2013.01); *A61F 13/00* (2013.01); *A61F 13/02* (2013.01);
(Continued)

(58) Field of Classification Search
CPC .......... A61M 25/02; A61M 2025/0253; A61M 2025/0266; A61M 25/0637;
(Continued)

(56) References Cited

U.S. PATENT DOCUMENTS

| 5,637,098 A | 6/1997 | Bierman |
| 7,232,427 B2 * | 6/2007 | Propp ................... A61M 25/02 |
| | | 128/849 |

(Continued)

FOREIGN PATENT DOCUMENTS

| WO | 9705920 A1 | 2/1997 |
| WO | 2011146781 A1 | 11/2011 |
| WO | 2018138324 A1 | 8/2018 |

*Primary Examiner* — Shefali D Patel

(74) *Attorney, Agent, or Firm* — The Webb Law Firm

(57) ABSTRACT

A catheter assembly may include a catheter adapter, a catheter, and a dressing to securely apply traction to the catheter where the catheter is disposed within a vasculature of a patient. The catheter adapter may include a proximal end, a distal end, and a lumen extending between the proximal end and the distal end. The catheter may extend from the distal end of the catheter adapter. The dressing may include a first section adjustably coupled to a second section. The first section may be configured to secure the catheter adapter and/or the catheter to the patient. The second section may be configured to be adjustably positioned relative to the first section to apply the traction to the catheter within the vasculature.

16 Claims, 10 Drawing Sheets

(52) U.S. Cl.
CPC .............. *A61F 2013/00412* (2013.01); *A61M 2025/0253* (2013.01); *A61M 2025/0266* (2013.01); *A61M 2025/0273* (2013.01)

(58) Field of Classification Search
CPC ...... A61M 25/0113; A61M 2025/0246; A61M 2210/12; A61M 2025/024; A61M 2025/0206; A61M 2209/088; A61M 2005/1586; A61M 2025/026; A61M 2025/0273; A61M 2209/08; A61M 2210/04; A61M 25/0097; A61F 13/00; A61F 2013/00412; A61F 13/0269; A61F 13/00051; A61F 13/02; A61F 13/0246; A61F 2013/00655
See application file for complete search history.

(56) References Cited

U.S. PATENT DOCUMENTS

| | | |
|---|---|---|
| 8,162,898 B1 | 4/2012 | Wright |
| 9,248,258 B2 * | 2/2016 | Roman ................. A61M 25/02 |
| 2007/0299381 A1 * | 12/2007 | Houchin ............... A61F 5/3723 |
| | | 602/5 |
| 2011/0106014 A1 * | 5/2011 | Helm, Jr. .............. A61M 25/02 |
| | | 604/178 |
| 2012/0016312 A1 | 1/2012 | Brown et al. |
| 2012/0089129 A1 | 4/2012 | Engelhardt |
| 2014/0228810 A1 * | 8/2014 | Rosenberg ............ A61M 25/02 |
| | | 604/513 |
| 2020/0038631 A1 | 2/2020 | O'Sullivan et al. |

* cited by examiner

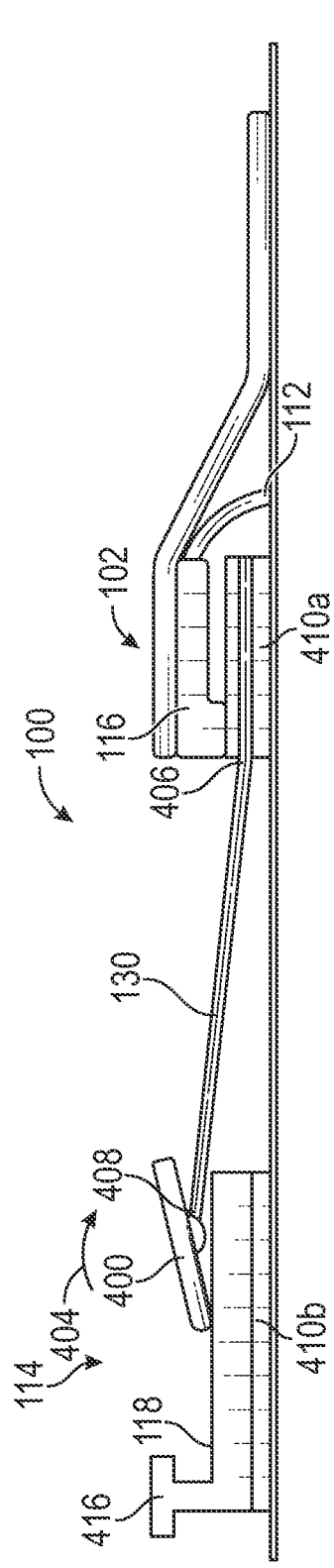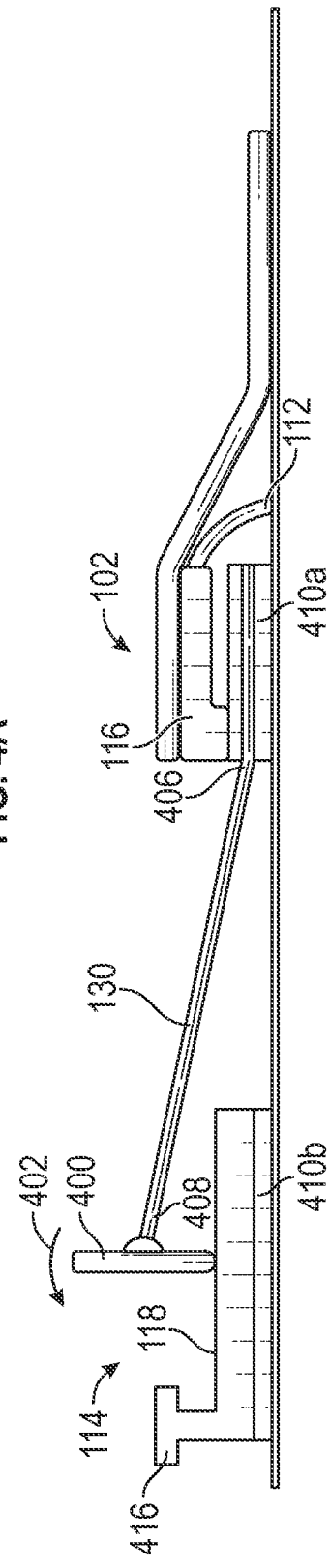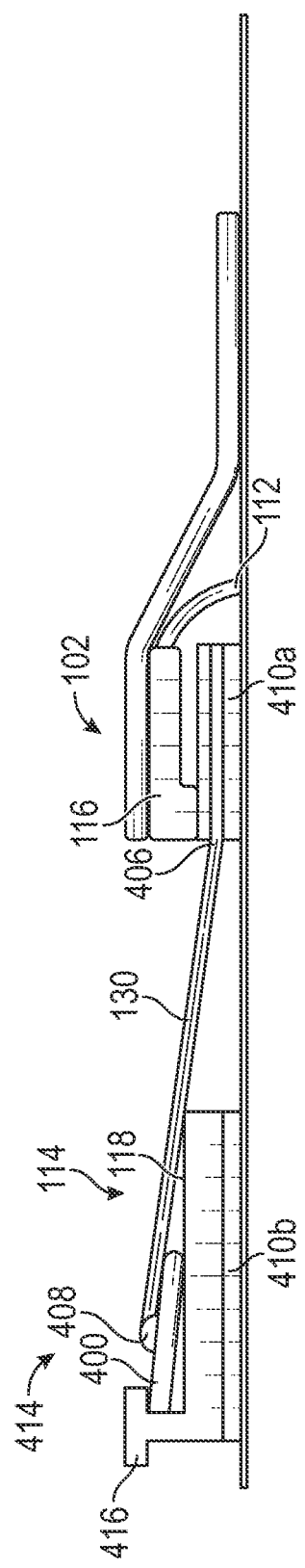

DRESSING-BASED TRACTION DEVICE AND RELATED SYSTEMS AND METHODS

RELATED APPLICATIONS

This application claims benefit of U.S. Provisional Patent Application No. 63/045,700, filed on Jun. 29, 2020, entitled DRESSING-BASED TRACTION DEVICE AND RELATED SYSTEMS AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient to obtain a blood sample.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Catheter functionality, however, may be impeded for several reasons. For example, when there is a prolonged dwelling time of the catheter within the vasculature, the ability for blood to flow under vacuum pressure decreases significantly. Occlusion of the catheter due to the presence of thrombus near the catheter tip and/or vein wall is a primary contributor to impeded fluid flow during the dwelling period of the catheter within the vasculature. As a result, while catheters are commonly used for blood collection at a time of catheter placement, they are less commonly used for blood collection during the catheter dwell period.

When a blood sample is desired during the catheter dwell period, an additional needle stick is typically used to provide vein access for blood collection, causing additional pain and anxiety for the patient as well as increased material costs. Applying traction to move or re-position the catheter tip within the vein may improve blood draw success. Considerable variation exists between traditional traction application techniques, however, all of which require manual manipulation of the catheter adapter. These methods are thus notoriously inconsistent and may lead to contamination and/or dislodgement of the catheter.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter assemblies used to infuse fluids and/or collect blood from the vasculature of a patient. Various complications and obstructions may impede fluid flow through the catheter, however, thus compromising catheter functionality and performance. For example, during a prolonged dwelling time of the catheter within the vasculature, the ability for blood to flow under vacuum pressure decreases significantly. Occlusion of the catheter due to the presence of thrombus near the catheter tip and/or vein wall is a primary contributor to impeded fluid flow during the dwelling period of the catheter within the vasculature. Applying traction to move or re-position the catheter tip within the vein may significantly improve catheter functionality and blood draw success.

In some embodiments, a catheter assembly to apply traction to a catheter may include a catheter adapter having a proximal end, a distal end, and a lumen extending along a longitudinal axis therebetween. A catheter may extend from the distal end of the catheter adapter. In some embodiments, a dressing may apply traction to the catheter when the catheter is disposed within a vasculature of a patient. In some embodiments, the dressing may include a first section adjustably coupled to a second section. Some embodiments of the first section may be configured to secure the catheter adapter and/or the catheter to the patient, while the second section may be configured to be adjustably secured relative to the first section. In this manner, some embodiments of the dressing may apply traction to the catheter within the vasculature.

In some embodiments, the first section and the second section may be independent of each other. Some embodiments of the first section include an aperture to receive at least a portion of the catheter adapter and/or the catheter. In some embodiments, the first section may include an adhesive to secure at least one of the catheter adapter and the catheter relative to the patient. Similarly, in some embodiments, the second section may be configured to be secured relative to the patient.

In some embodiments, the catheter assembly may further include an adjustment element to adjustably couple the first section to the second section. Some embodiments of the adjustment element may be releasable to decouple the first section and the second section. In some embodiments, the adjustment element may include one or more tethers. Each tether may include a first end coupled to the first section and a second end coupled to the second section. In some embodiments, each tether may be selectively tightened to apply traction to the catheter.

In some embodiments, the adjustment element may include a first finger grip coupled to the first section and/or the catheter adapter and a second finger grip coupled to the second section. In this manner, some embodiments enable the second section to be manually adjusted relative to the first section to apply traction to the catheter. In some embodiments, the adjustment element may include at least one arm extending between the first section and the second section. In some embodiments, manipulating a position of the one or more arms may adjust a distance between the first section and the second section, thereby applying traction to the catheter.

Some embodiments of the catheter assembly may further include a lock element to secure the distance between the first section and the second section to maintain traction on the catheter. In some embodiments, the lock element may mechanically engage at least a portion of the one or more arms to maintain traction on the catheter.

In some embodiments, the arms may include one or more joints. In some embodiments, depressing the arm inwardly towards the longitudinal axis may apply traction to the catheter.

In some embodiments, each of the one or more arms may include a switch portion movably coupled to an extension portion. Moving the switch portion in a direction parallel to the longitudinal axis and away from the first section in accordance with some embodiments may shorten the distance between the first section and the second section to thereby apply traction to the catheter. In some embodiments, the adjustment element may include a dial feature coupled to the arm. In some embodiments, rotating the dial feature may adjust the distance between the first section and the second section to apply traction to the catheter.

In some embodiments, the catheter assembly to apply traction to a catheter may include the catheter adapter, the catheter extending from the distal end of the catheter adapter, and a stabilizer element. Some embodiments of the stabilizer element may be configured to slidably engage the catheter adapter element. In some embodiments, the stabilizer element may include one or more tracks disposed substantially parallel to the longitudinal axis. Some embodiments of the stabilizer element may thus maintain a lateral position of the catheter adapter while enabling the catheter adapter to slide parallel to the longitudinal axis along the track.

In some embodiments, the catheter adapter may include one or more engagement features extending parallel to the longitudinal axis. Some embodiments of the engagement feature may slidably engage the one or more tracks. Some embodiments of the stabilizer element may be configured to adjust an angle of the catheter adapter relative to the patient. In this manner, some embodiments of the stabilizer element apply traction to the catheter within the vasculature.

In some embodiments, the catheter assembly to apply traction to the catheter may include the catheter adapter, the catheter extending from the distal end of the catheter adapter, and a dressing configured to secure the catheter adapter and/or the catheter relative to the patient. In some embodiments, the dressing may include an incline mechanism configured to adjust an angle of the catheter adapter relative to the stabilizer element to apply traction to the catheter within the vasculature. In some embodiments, the incline mechanism may include a flexible linkage element to enable manual adjustment of the angle of the catheter adapter relative to the stabilizer element.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4A is a side perspective view of another example catheter assembly including another example dressing according to some embodiments;

FIG. 4B is a side perspective view of the catheter assembly of FIG. 4A, illustrating adjustment of the dressing according to some embodiments;

FIG. 4C is a side perspective view of the catheter assembly of FIG. 4A, illustrating the dressing positioned to apply traction to the catheter according to some embodiments;

DETAILED DESCRIPTION

As used in this specification, the term "distal" refers to a direction away from a clinician who would place the device into contact with a patient, and nearer to the patient. The term "proximal" refers to a direction nearer to the clinician who would place the device into contact with the patient, and farther away from the patient. Thus, for example, the end of a catheter first touching the body of the patient is the distal end, while the opposite end of the catheter is the proximal end of the catheter.

As set forth above, various complications and obstructions may impede fluid flow through the catheter, particularly when there is a prolonged dwelling period of the catheter within the vasculature of the patient. Occlusion of the catheter due to thrombus near the catheter tip and/or vein wall is a primary contributor to impeded fluid flow through the catheter. Applying traction to move or re-position the catheter tip within the vein may significantly improve catheter functionality and blood draw success.

Clinicians, however, tend to use whichever traction application technique they feel most comfortable with, leading to a large degree of variation in traction application techniques and outcomes. In addition, many traction application methods involve manipulation of the catheter adapter with concurrent risks of contamination and dislodgement of the catheter.

The present disclosure describes several concepts to allow consistent application of traction through a dressing placed over the catheter. Traction applied through the dressing may avoid manipulation of the catheter, thereby promoting longevity of an indwelling catheter by minimizing the potential for contamination and dislodgement. Some embodiments provided herein also facilitate application of traction in a consistent manner to increase the likelihood of blood draw success.

Figure 1:
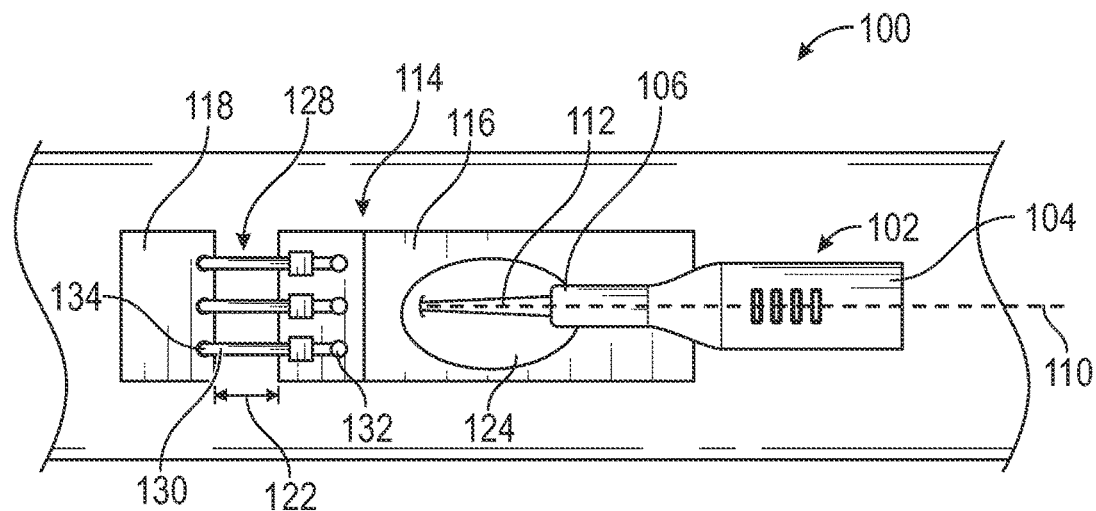
FIG. 1 is an upper perspective view of an example catheter assembly including an example dressing to apply traction to a catheter according to some embodiments.

Referring now to FIG. 1, in some embodiments, a catheter assembly 100 may be configured to apply traction to a catheter 112 to create a clear pathway for fluid flow. In some embodiments, the catheter assembly 100 may include a catheter adapter 102 having a proximal end 104, a distal end 106, and an interior lumen extending along a longitudinal axis 110 therebetween.

The catheter 112 may extend from the distal end 106 of the catheter adapter 102. In some embodiments, the catheter 112 may be used for blood collection, fluid delivery, patient or device monitoring, or other clinical needs. In some embodiments, the catheter 112 may include, for example, a peripheral IV catheter, a peripherally-inserted central catheter, or a midline catheter. In some embodiments, the catheter 112 may have been previously inserted into the vasculature of the patient and may be dwelling within the vasculature.

In some embodiments, a dressing 114 may securely apply traction to the catheter 112 while the catheter 112 is disposed within the vasculature of the patient. In some embodiments, the dressing 114 may include an adhesive 126 to secure the dressing 114 to the patient. In some embodiments, the dressing 114 may include a two-piece or two-section dressing 114 connected by an adjustment element 128. In some embodiments, the dressing 114 may include more than two sections, and may be connected by one or more adjustment elements 128, such as an adjustable tether 130 or other suitable fastener or strap.

In some embodiments, each or some of the sections of the dressing 114 may be spaced apart from each other by a distance 122. The distance 122 between the sections of the dressing 114 may be selected to optimize application of traction to the catheter 112. For example, in operation, some embodiments may apply traction to the catheter 112 by adjusting the distance 122 between two or more of the dressing 114 pieces or sections. In some embodiments, the distance 122 between the dressing 114 sections may be manually or automatically adjusted by the adjustment element 128. In some embodiments, adjusting the distance 122 between the dressing 114 sections in this manner may exert tension between the dressing 114 sections to apply traction to the catheter 112.

In some embodiments, the dressing 114 may include a first section 116 adjustably coupled to a second section 118. In some embodiments, an adjustment element 128 may adjustably couple the first section 116 to the second section 118. The adjustment element 128 may include, for example, a tether, a winch, a ratchet, a pulley, a dial, a screw, a cable tie, or other suitable tensioning device or mechanism. Some embodiments of the adjustment element 128 may be releasable and/or removable to decouple the first and second sections 116, 118.

In some embodiments, the first section 116 may be independent of the second section 118. Some embodiments of the first section 116 may be configured to secure and/or maintain a position of the catheter adapter 102 and/or the catheter 112 to the patient via an adhesive 126, for example. In some embodiments, the first section 116 may include an aperture 124 or other suitable feature or mechanism to maintain the catheter adapter 102 and/or the catheter 112 in a substantially fixed position relative to the patient.

In some embodiments, the second section 118 may be adjustably positioned and/or secured relative to the first section 116 to apply traction to the catheter 112 within the vasculature. In some embodiments, the second section 118 may include an adhesive 126 or other suitable device or mechanism to secure and/or maintain the position of the second section 118 relative to the patient. Some embodiments of the second section 118 may include a securing device or mechanism to secure and/or maintain the position of the second section 118 relative to the first section 116.

In some embodiments, the position of the second section 118 relative to the first section 116 may be adjusted by the adjustment element 128. In some embodiments, as shown in FIG. 1, the adjustment element 128 may include one or more tethers 130 to couple the dressing 114 sections 116, 118 together. In some embodiments, a first end 132 of the tether 130 may be coupled to the first section 116 and a second end 134 of the tether 130 may be coupled to the second section 118.

In some embodiments, the tethers 130 may be configured to be adjusted individually such that each tether 130 individually pulls traction on the catheter 112. In some embodiments, the tethers 130 may be configured to be adjusted collectively as a single unit to pull traction on the catheter 112. In some embodiments, each tether 130 may pull traction on the catheter 112 in either a proximal or distal direction.

In some embodiments, tightening the tethers 130 may pull the skin of the patient such that the tip 120 of the catheter 112 may be re-oriented within the vasculature. In some embodiments, repositioning the tip 120 of the catheter 112 within the vasculature in this manner may clear 130 a fluid path for infusion of fluid or medications or blood withdrawal. In some embodiments, the adjustment element 128 may be automatically or manually adjusted or loosened to return the dressing 114 to its initial position, thereby releasing traction on the catheter 112.

Figure 2A:
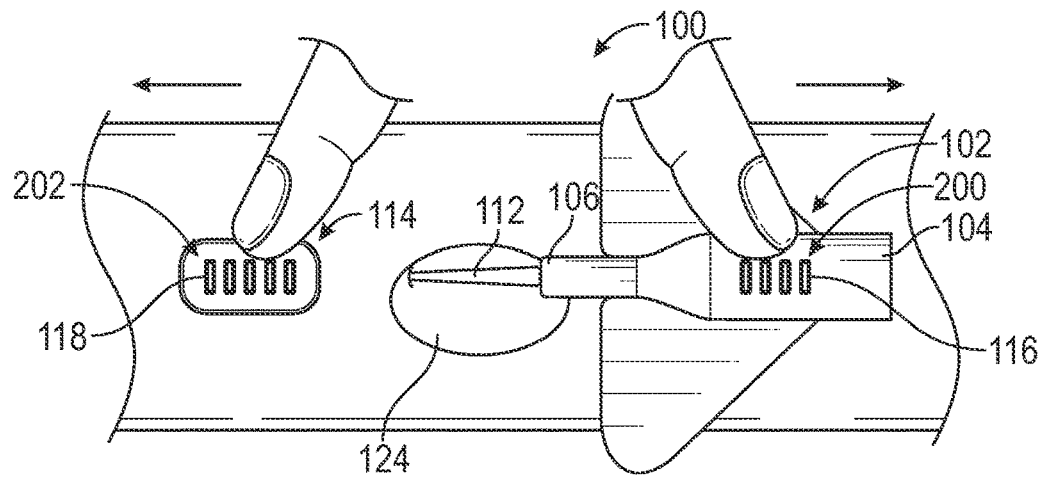
FIG. 2A is an upper perspective view of another example catheter assembly and example dressing to apply traction to the catheter according to some embodiments.
Figure 2B:
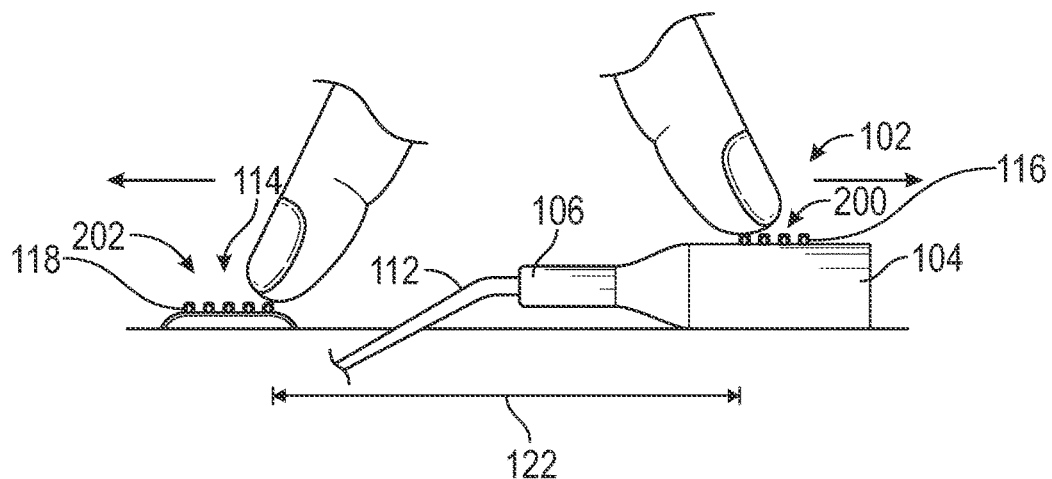
FIG. 2B is a side perspective view of the catheter assembly of FIG. 2A.

Referring now to FIG. 2, in some embodiments, the adjustment element 128 may include one or more finger grips 200, 202 to facilitate manual adjustment of the second section 118 of the dressing 114 relative to the first section 116 of the dressing 114. In some embodiments, a first finger grip 200 may be coupled to the first section 116 and a second finger grip 202 may be coupled to the second section 118. In some embodiments, the first section 116 and the second section 118 of the dressing 114 may be monolithically formed as a single unit. Some embodiments of the first finger grip 200 or the second finger grip 202 may be coupled to the catheter adapter 102.

In operation, the clinician may utilize the first finger grip 200 to adjust or maintain the position of the first section 116 relative to the patient while utilizing the second finger grip 202 to adjust or maintain the position of the second section 118 relative to the first section 116. In some embodiments, the first finger grip 200 may be utilized to maintain the position of the first section 116 while the position of the second section 118 may be adjusted relative to the first section 116 via the second finger grip 202.

In some embodiments, the first finger grip 200 may be utilized to adjust the position of the first section 116 in a proximal or distal direction while the position of the second section 118 may be simultaneously adjusted in an opposite direction via the second finger grip 202. In some embodiments, the first and/or the second finger grips 200, 202 may be utilized to adjust a tilt, incline, or other position or orientation of the first section 116 relative to the second section 118. In some embodiments, utilizing one or more of the finger grips 200, 202 to manually adjust the position of the first section 116 relative to the second section 118 in this manner may apply traction to the catheter 112 to reposition the tip 120 of the catheter 112 within the vasculature and thereby open a fluid path.

Referring now to FIG. 3, in some embodiments, the adjustment element 128 may include one or more arms 300 extending between the first section 116 and the second section 118. In some embodiments, manipulating a position and/or orientation of the one or more arms 300 may adjust the distance 122 between the first section 116 and the second section 118, thereby applying traction to the catheter 112.

Figure 3A:
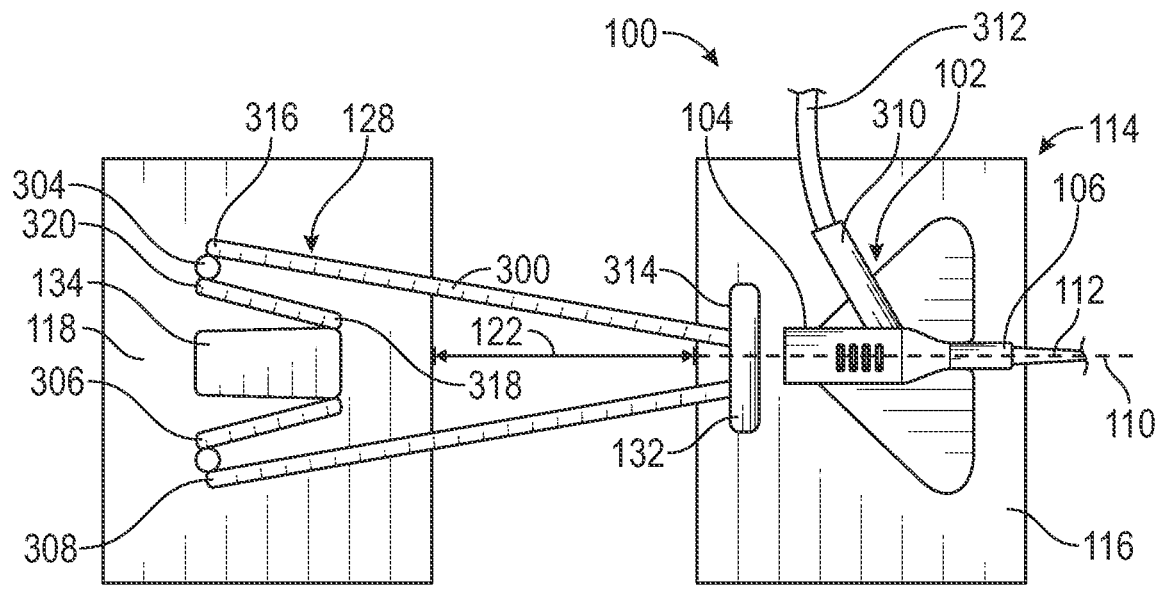
FIG. 3A is an upper perspective view of an example catheter assembly comprising an example dressing including a toggle element according to some embodiments.

Some embodiments of the arm 300 may include one or more joints 304 to enable relative movement between arm 300 segments. As shown in FIG. 3A, in some embodiments, the arm 300 may include a switch portion 306 movably coupled to an extension portion 308. In some embodiments, the switch portion 306 may be coupled to the extension portion 308 via the joint 304. In this manner, in some embodiments, the switch portion 306 and the extension portion 308 may move freely with respect to each other. In some embodiments, the joint 304 may allow limited relative movement between the switch portion 306 and the extension portion 308.

In some embodiments, the joint 304 may include a suitable locking device or mechanism to selectively secure a relative position of the switch portion 306 and the extension portion 308. In some embodiments, the arm 300 may include a locking device or mechanism to secure the distance 122 between the first section 116 and the second section 118 to maintain traction on the catheter 112. In some embodiments, the lock device or mechanism may mechanically engage at least a portion of the one or more arms 300 to maintain traction on the catheter 112.

In some embodiments, a first end 314 of the extension portion 308 may be coupled to the first section 116 of the dressing 114 a second end 316 of the extension portion 308 may be coupled to the joint 304. Similarly, in some embodiments, the switch portion 306 may include a first end 318 coupled to the second section 118 and a second end 320 coupled to the joint 304. In some embodiments, the first end 314 may be coupled to the first section 116 via any suitable fastening device or adhesive. In some embodiments, more than one extension portion 308 may be joined together at their first end 314 and coupled to the first section 116. In some embodiments, the extension portion 308 of each arm 300 may be individually coupled to the first section 116.

In any case, in some embodiments, the first section 116 of the dressing 114 may be further configured to secure the catheter adapter 102 relative to the patient. In some embodiments, the catheter adapter 102 may include a side port 310 coupled to an extension set 312 to facilitate fluid infusion and/or blood withdrawal. In some embodiments, the catheter adapter 102 may be substantially aligned with the extension portions 308 of the arms 300 along the longitudinal axis 110. In this manner, in some embodiments, actuation of the arms 300 may pull traction on the catheter 112 extending from the distal end 106 of the catheter adapter 102. Some embodiments of the one or more arms 300 may act as a toggle such that actuating the arms 300 may adjust the distance 122 between the first section 116 and the second section 118 of the dressing 114.

Figure 3B:
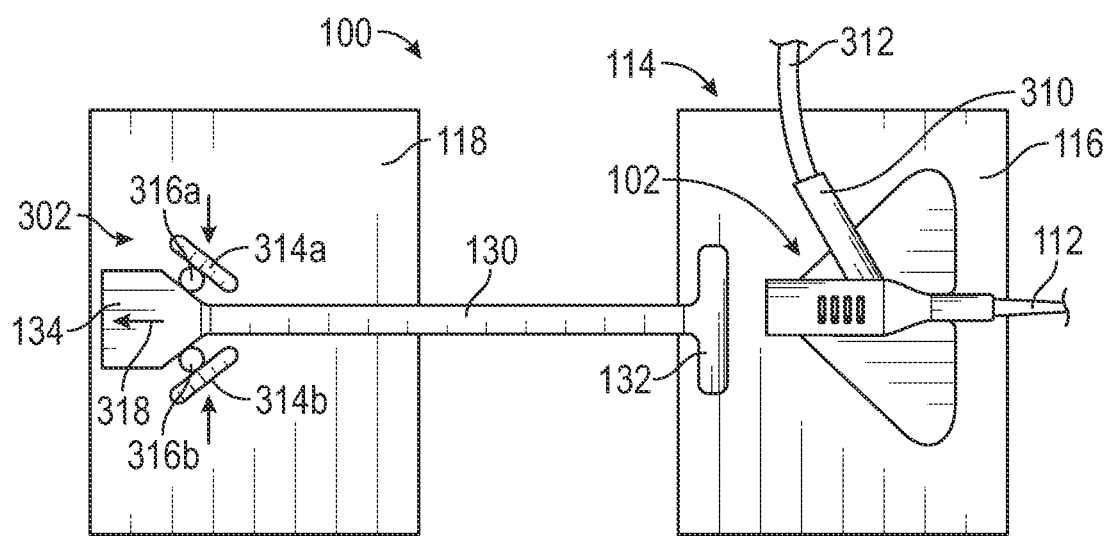
FIG. 3B is an upper perspective view of the catheter assembly of FIG. 3A, illustrating the dressing positioned to apply traction to the catheter according to some embodiments.

Referring now to FIG. 3B, some embodiments may include a sliding arm 300 or cam element 302 to mechanically link the first section 116 to the second section 118. As discussed above, in some embodiments, a tether 130 may be couple the first section 116 to the second section 118. Specifically, in some embodiments, the first end 132 of the tether 130 may be coupled to or integrated with the first section 116 and the second end 134 of the tether 130 may be coupled to or integrated with the second section 118.

Some embodiments of the cam element 302 may include tabs 314a, 314b disposed on opposing sides of the second end 134 of the tether 130. The tabs 314a, 314b may be coupled to the second end 134 of the tether 130 via rollers 316a, 316b or any suitable sliding element or mechanism. In operation, in some embodiments, the second end 134 of the tether 130 may taper in a proximal direction. In this manner, the tabs 314a, 314b may be squeezed inwardly to move the tabs 314a, 314b toward each other in the proximal direction while simultaneously urging the second end 134 of the tether 130 in a distal direction 318. This movement of the second end 134 of the tether 130 relative to the first end 132 of the tether 130 may decrease a distance between the first section 116 and the second section 118 of the dressing 114, thus pulling traction on the catheter 112 extending from the distal end 106 of the catheter adapter 102.

Referring now to FIGS. 4A-C, in some embodiments, the adjustment element 128 may include a tether 130 coupled to a toggle element 400. In some embodiments, one end 406 of the tether 130 may be coupled to the first section 116 of the dressing 114 and an opposite end 408 of the tether 130 may be coupled to the toggle element 400. In some embodiments, the toggle element 400 may be coupled to the second section 118 of the dressing 114.

Some embodiments may include a first base element 410a coupled to the first section 116 and a second base element 410b coupled to the second section 118 of the dressing 114. In some embodiments, the first base element 410a may be coupled to one end 406 of the tether 130 and may include a size and/or shape configured to receive and retain the catheter adapter 102 in a fixed position relative to the first section 116. The base element 410 coupled to the second section 118 may include a feature or mechanism to retain the toggle element 400 such that the toggle element 400 may be moved between a first position 412 and a second position 414. In some embodiments, the opposite end of the tether 130 may be coupled to a midpoint of the toggle element 400. In some embodiments, the toggle element may be rod-shaped and may be configured to move bi-directionally to apply traction to the catheter 112.

For example, in some embodiments, the toggle element 400 may be configured to pivot in an axial direction substantially corresponding to the longitudinal axis 110. In this manner, in some embodiments, the toggle element 400 may pivot to a first axial position 412 of the toggle element 400 to apply traction to the catheter 112 and to a second axial position 414 to release traction from the catheter 112. In some embodiments, the toggle element 400 may be moved between the first axial position 412 and the second axial position 414 to gradually apply or release traction from the catheter 112 to adjust the position of the tip 120 of the catheter 112 within the vasculature. In some embodiments, the toggle element 400 may be secured into position by a lock element such as a latch or other suitable device.

Figure 5A:
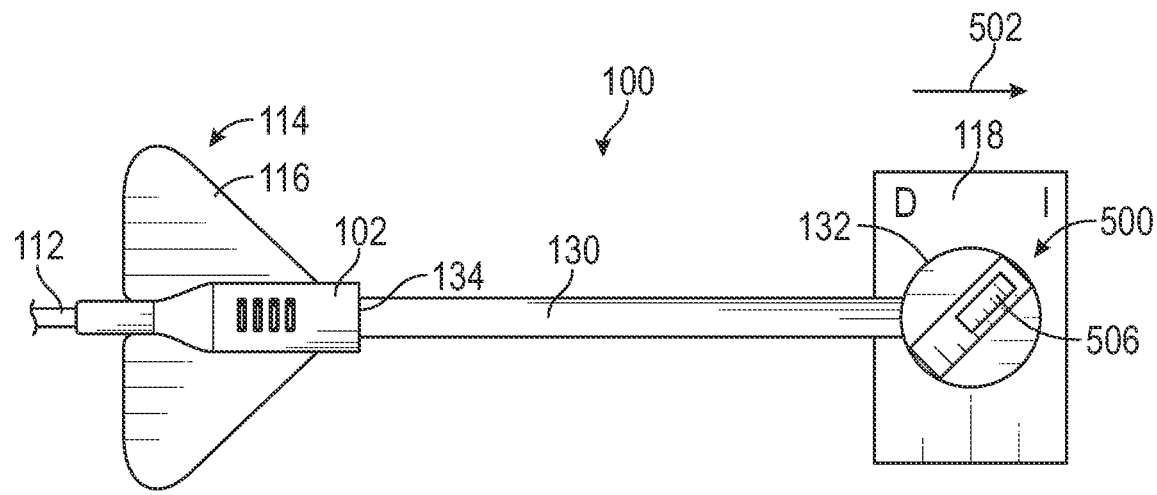
FIG. 5A is an upper perspective view of another example catheter assembly including another example dressing according to some embodiments.
Figure 5B:
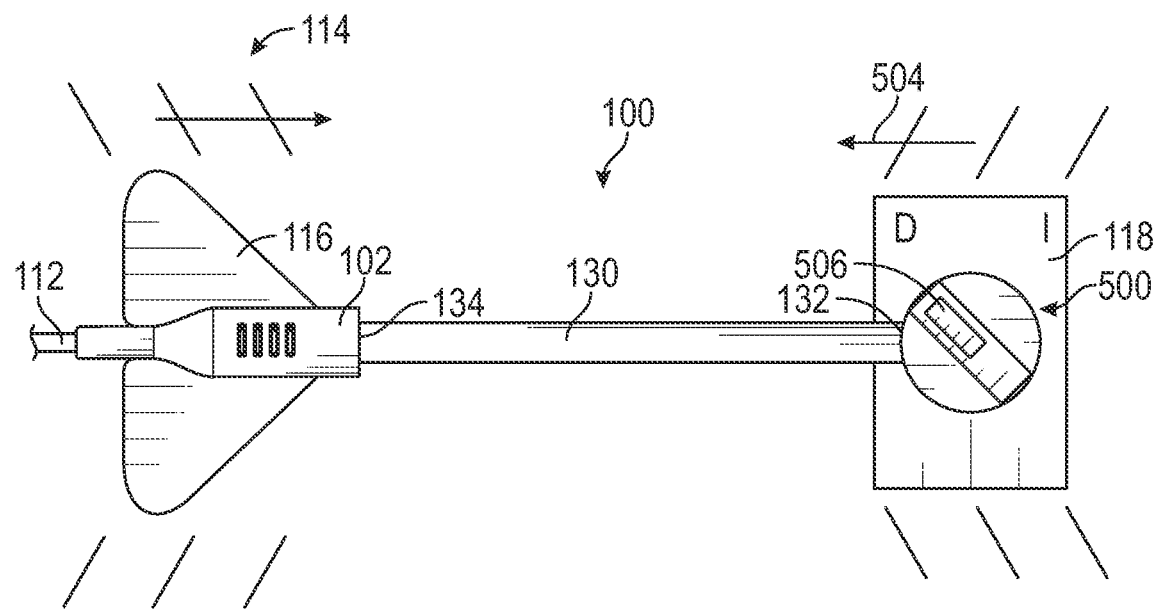
FIG. 5B is an upper perspective view of the catheter assembly of FIG. 5A, illustrating the dressing positioned to apply traction to the catheter according to some embodiments.

Referring now to FIG. 5, some embodiments of the adjustment element 128 may include a dial feature 500 configured to adjust the distance 122 between the first section 116 and the second section 118 to apply traction to the catheter 112. In some embodiments, the dial feature 500 may include, for example, a toggle, a ratchet, a pulley, or other suitable device.

In some embodiments, the catheter adapter 102 may be coupled to the first section 116 and the dial feature 500 may be coupled to the second section 118. In some embodiments, the tether 130 may extend between the catheter adapter 102 and the dial feature 500. In some embodiments, the first end 132 of the tether 130 may be wound around the dial feature 500 such that the dial feature 500 may be manipulated to adjust a length of the tether 130. Specifically, in some embodiments, an indicator 506 on the dial feature 500 may be moved in a first direction 502 to wind the tether 130 tighter, thereby shortening the distance 122 between the first section 116 and the second section 118 to apply traction to the catheter 112. Similarly, the indicator 506 may be moved in a second direction 504 to unwind the tether 130 to lengthen the distance 122 and release traction on the catheter 112. Of course, in some embodiments, the tether 130 may be secured to an intermediary element between the first section 118 and the catheter adapter 102 and/or between the second section 118 and the dial feature 500.

Figure 6A:
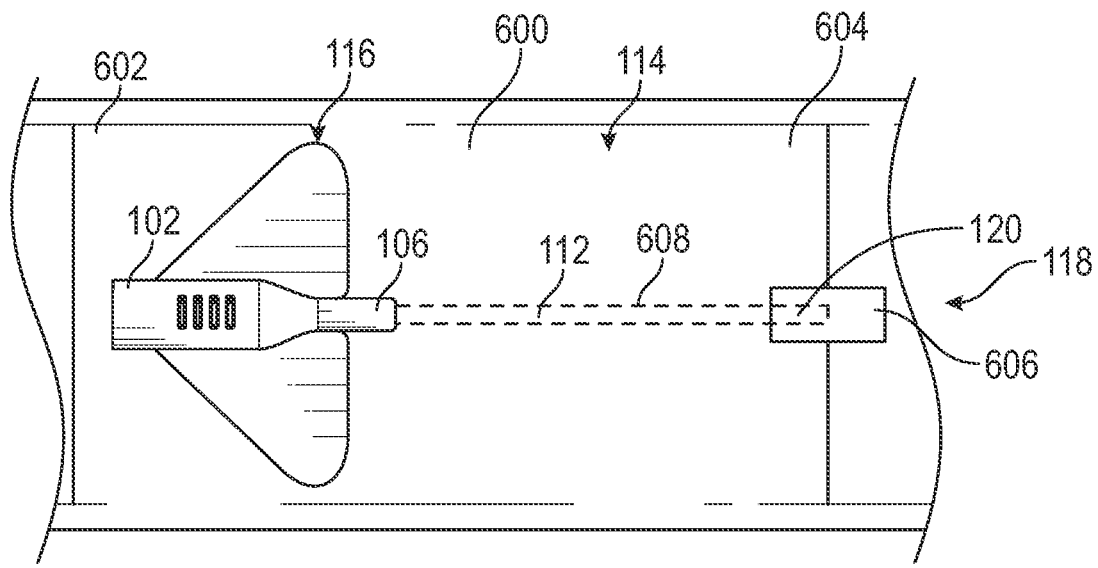
FIG. 6A is an upper perspective view of another example catheter assembly including another example dressing according to some embodiments.
Figure 6B:
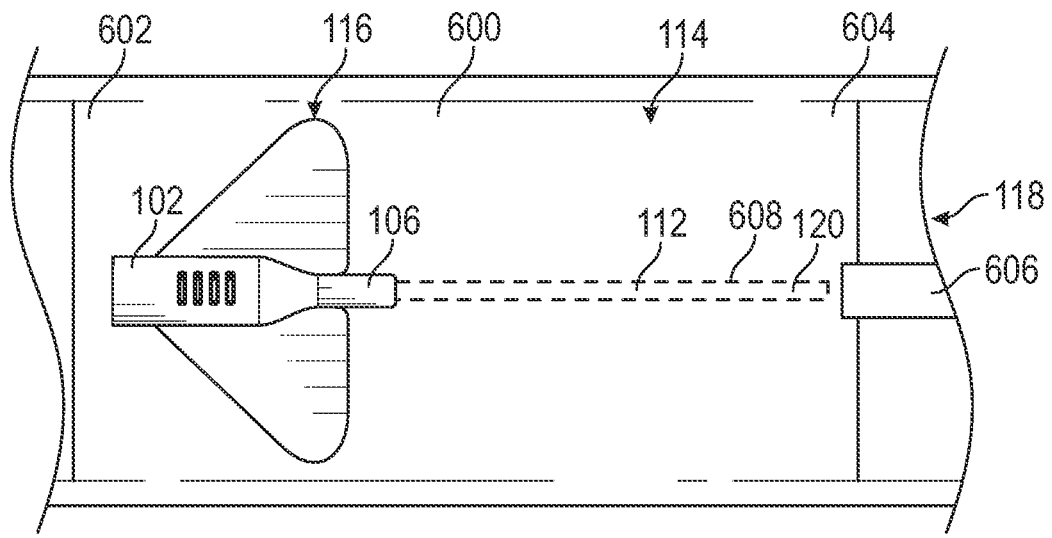
FIG. 6B is an upper perspective view of the catheter assembly of FIG. 6A positioned to apply traction to the catheter according to some embodiments.

Referring now to FIGS. 6A and 6B, in some embodiments, the catheter assembly 100 may include a dressing 114 where the first section 116 includes a pad 600 to secure the catheter adapter 102 relative to the patient. The pad 600 may include an aperture, adhesive, and/or other suitable securing feature to receive the catheter adapter 102 and to secure the catheter adapter 102 relative to the pad 600 and the patient. In some embodiments, the catheter 112 may extend from the distal end 106 of the catheter adapter 102, through the aperture or other pad 600 feature, and into the vasculature of the patient. In some embodiments, the pad 600 may have a length sufficient to extend over a length of the catheter 112 within the vasculature. In some embodiments, the pad 600 may include markings 608 to indicate an approximate location of the catheter 112 beneath the pad 600.

In some embodiments, the second section 118 may include an isolated section of the dressing 114, such as a tab 606 coupled to a distal end 604 of the pad 600. In some embodiments, the pad 600 and the tab 606 may be monolithically formed as a single unit. In operation, the tab 606 may be pulled in a distal direction relative to the distal end 106 of the catheter adapter 102 to apply traction to the catheter 112. In some embodiments, the tab 606 may include an adhesive or other suitable mechanism to enable the tab 606 to be selectively moved in the distal direction and secured in place to apply continuous traction to the catheter 112. In some embodiments, the markings 608 and/or the tab 606 may facilitate blood withdrawal by indicating a desired or optimal location for a clinician to apply pressure for blood withdrawal.

Figure 7A:
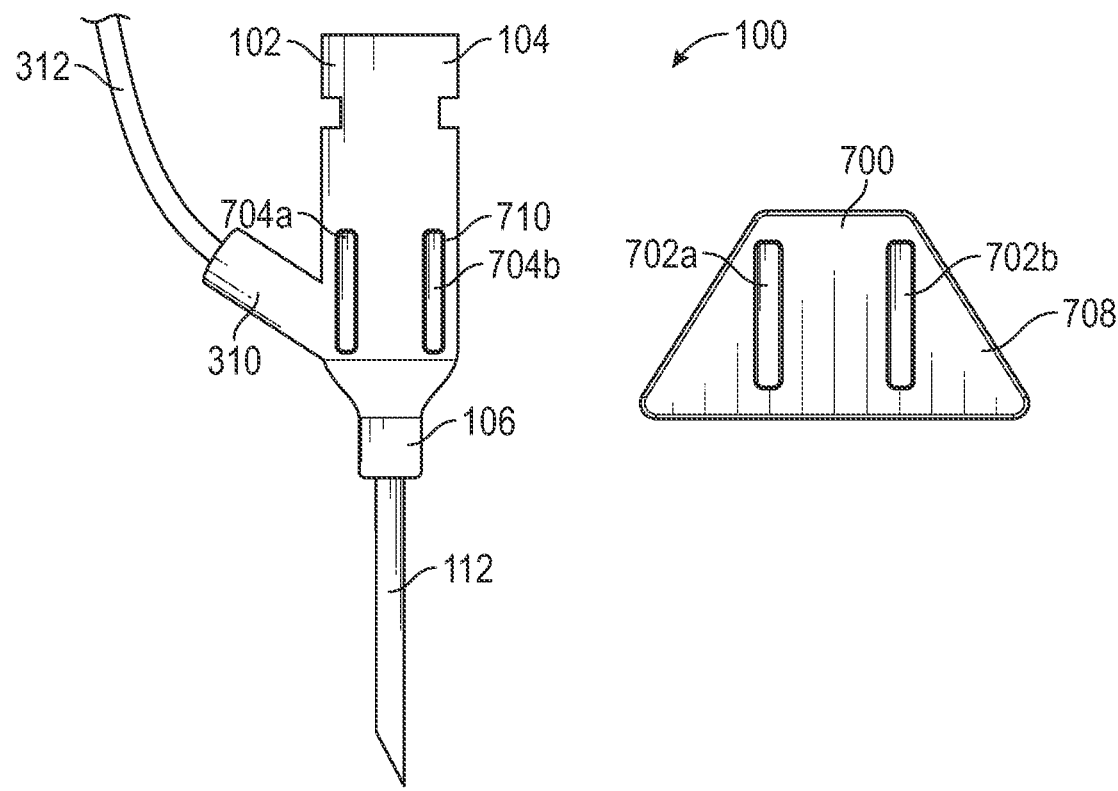
FIG. 7A is an exploded upper perspective view of an example catheter assembly and an example dressing including an example stationary base element according to some embodiments.

Referring now to FIG. 7A, in some embodiments, the catheter assembly 100 to apply traction to the catheter 112 may include the catheter adapter 102, the catheter 112 extending from the distal end 106 of the catheter adapter 102, and a stabilizer element 700. Some embodiments of the stabilizer element 700 may be configured to slidably engage the catheter adapter 102.

For example, in some embodiments, one or more engagement features 704a, 704b may be disposed on a bottom surface of the catheter adapter 102 and may extend in a direction parallel to the longitudinal axis 110. In some embodiments, the stabilizer element 700 may be substantially planar and may include wings 708 configured to extend from the catheter adapter 102 in a transverse direction relative to the longitudinal axis 110. In some embodiments, the engagement features 704a, 704b may include slots 710 disposed in the bottom surface of the catheter adapter 102. Some embodiments of the wings 708 may be tapered to facilitate threading the stabilizer element 700 through the slots 710 such that the stabilizer element 700 may engage with the catheter adapter 102.

In some embodiments, the stabilizer element 700 may include one or more tracks 702a, 702b extending in a direction substantially parallel to the longitudinal axis 110 of the catheter adapter 102 when the stabilizer element 700 is engaged with the catheter adapter 102. In some embodiments, engaging the stabilizer element 700 with the catheter adapter 102 via the slots 710 may cause the slots 710 to align with the tracks 702 of the stabilizer element 700. In some embodiments, the tracks 702 may include protrusions, ridges, ribs, slots, recesses, indents, or other suitable features to engage the engagement feature 704 of the catheter adapter 102. Likewise, some embodiments of the engagement feature 704 may include protrusions, ridges, ribs, slots, recesses, indents, or other suitable features to engage the one or more tracks 702 of the stabilizer element 700. In any case, in some embodiments, the one or more engagement features 704 may engage the one or more tracks 702 to secure the stabilizer element 700 to the catheter adapter 102.

Figure 7B:
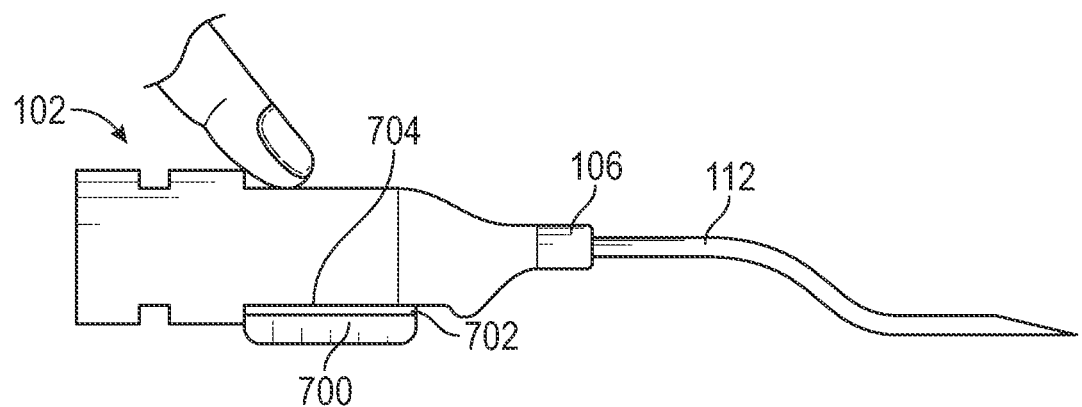
FIG. 7B is a side perspective view of the catheter assembly of FIG. 7A.
Figure 7C:
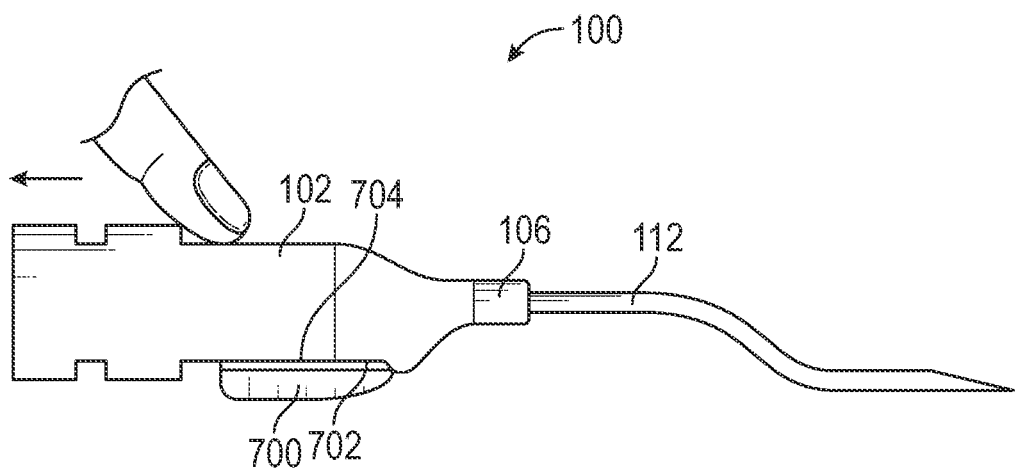
FIG. 7C is a side perspective view of the catheter assembly of FIG. 7A positioned to apply traction to the catheter.

Referring now to FIGS. 7B and 7C, some embodiments of the engagement features or slots 710 may slidably engage the tracks 702 of the stabilizer element 700 such that the catheter adapter 102 may move horizontally relative to the stabilizer element 700. In some embodiments, the stabilizer element 700 may include a size and/or contour to complement the size and/or contour of the catheter adapter 102, thereby promoting a snug fit at each end of the catheter adapter 102 and preventing undesired movement between the stabilizer element 700 and the catheter adapter 102. Some embodiments of the catheter adapter 102 may further include tubing or another suitable device or element to prevent relative movement between the catheter adapter 102 and the catheter 112 or outer sleeve of the catheter 112. In this manner, some embodiments may maintain a lateral position of the catheter adapter 102 relative to the stabilizer element 700 while enabling the catheter adapter 102 to slide along the longitudinal axis 110. Some embodiments may further include a release button or other suitable mechanism to selectively release the catheter adapter 102 from the stabilizer element 700.

Figure 7D:
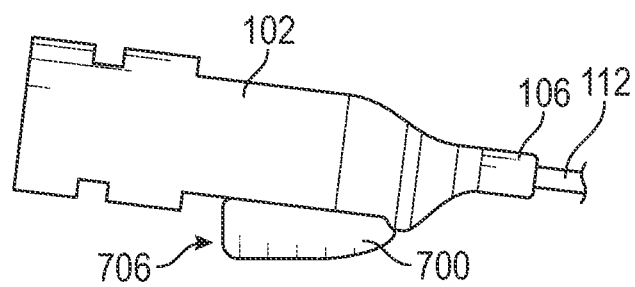
FIG. 7D is a side perspective view of the catheter assembly of FIG. 7A including another example stationary base element according to some embodiments.

Referring now to FIG. 7D, some embodiments may be configured such that the catheter adapter 102 may be adjusted in a vertical and/or horizontal direction relative to the stabilizer element 700. For example, in some embodiments, the stabilizer element 700 may include an angled contour 706 or other suitable shape or mechanism to adjust a vertical elevation, incline angle, and/or orientation of the catheter adapter 102 relative to the stabilizer element 700. In this manner, some embodiments of the catheter adapter 102 may be configured such that adjustment of the vertical angle and/or orientation of the catheter adapter 102 relative to the stabilizer element 700 may apply traction to the catheter 112 within the vasculature. For example, as shown in FIG. 7D, in some embodiments the catheter adapter 102 may be adjusted such that the distal end 106 of the catheter adapter 102 tilts downward toward the patient and the proximal end 104 of the catheter adapter 102 angles upward.

Figure 8:
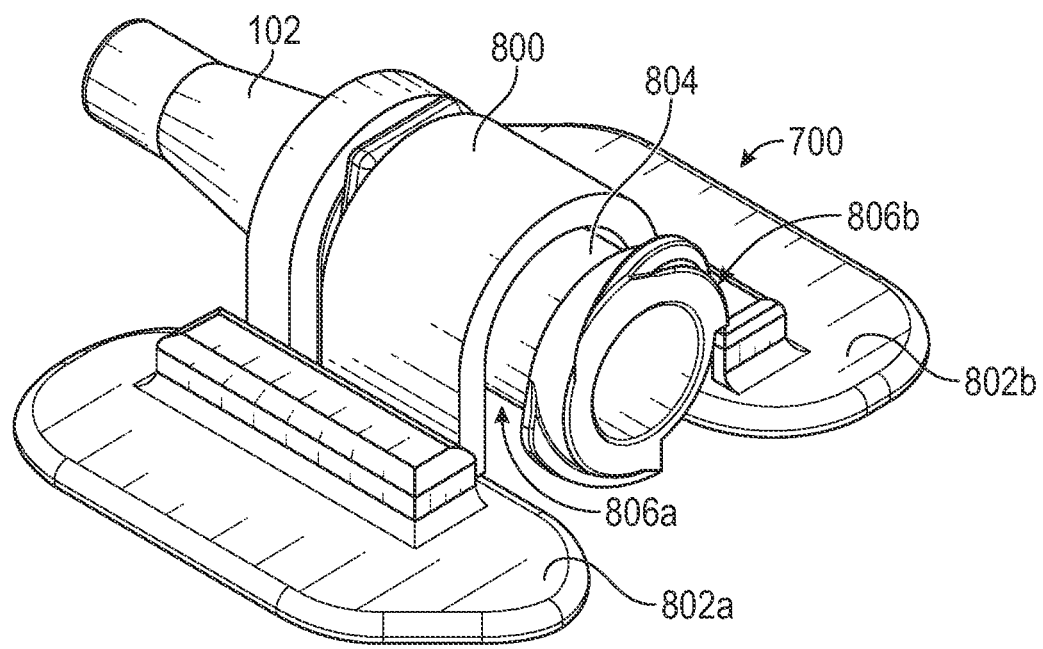
FIG. 8 is a perspective view of an example catheter adapter and an example stabilizer element in accordance with some embodiments.

Referring now to FIG. 8, alternative embodiments of the stabilizer element 700 may include a flexible linkage element 800 to adjust a vertical elevation, angle, and/or orientation of the catheter adapter 102 relative to the stabilizer element 700. As shown, some embodiments of the flexible linkage element 800 may adjustably couple the catheter adapter 102 to one or more base portions 802 of the stabilizer element 700. In some embodiments, the flexible linkage element 800 may allow a user to manually adjust or the vertical orientation and/or angle of the catheter adapter 102 relative to the base portion 802 in a controlled manner to apply traction to the catheter 112.

In some embodiments, the flexible linkage element 800 may include, for example, rubber, an elastomeric polymer, or other suitable flexible or resilient material to allow controlled movement of the catheter adapter 102 relative to the base portion 802 of the stabilizer element 700. In some embodiments, the flexible linkage element 800 may include a short piece of tubing or one or more straps coupled to the base portion 802 of the stabilizer element 700 and extending over a top surface 804 of catheter adapter 102 to retain the catheter adapter 102 with respect thereto.

In some embodiments, one end of the flexible linkage element 800 may be coupled to a first base portion 802*a* of the stabilizer element 700 and a second end of the flexible linkage element 800 may be coupled to a second base portion 802*b* of the stabilizer element 700. In some embodiments, the first base portion 802 may be disposed on a first side 806*a* of the catheter adapter 102 and the second base portion 802*b* may be disposed on a second side 806*b* of the catheter adapter 102. Some embodiments of the flexible linkage element 800 may include a shape or contour to accommodate various exterior features of the catheter adapter 102.

Figure 9:
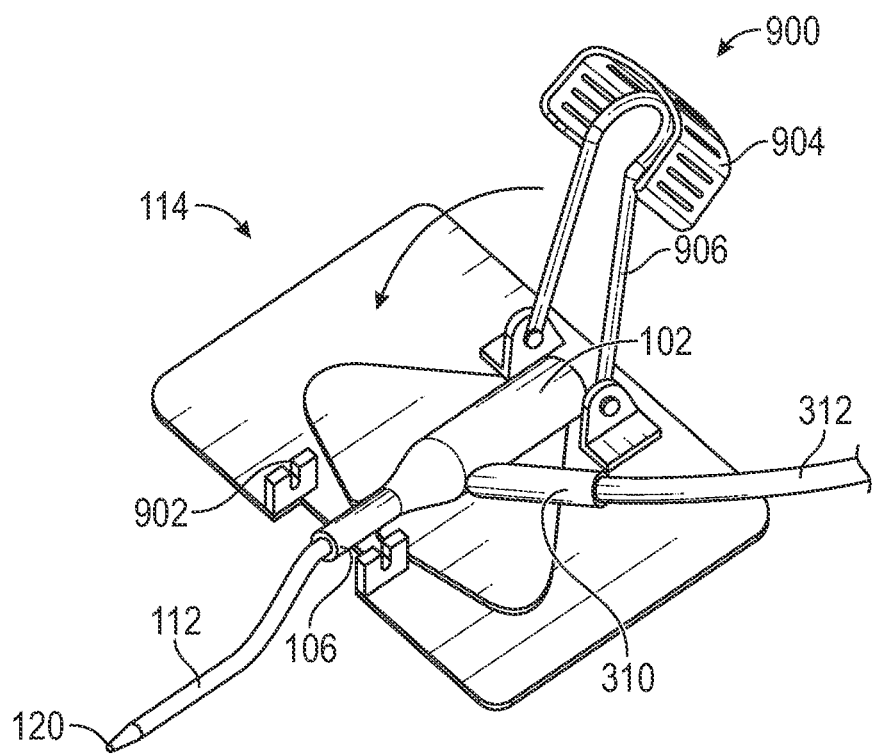
FIG. 9 is an upper perspective view of another example catheter assembly having another example dressing according to some embodiments.

Referring now to FIG. 9, some embodiments of a catheter assembly 100 may include a dressing 114 coupled to an incline device 900 or other suitable feature to automatically adjust the angle of the catheter adapter 102 relative to the dressing 114. In some embodiments, the dressing 114 may include a foam pad-style dressing 114 having an indentation or other suitable stabilization feature for stabilizing the catheter adapter 102 therein. For example, some embodiments may include a dressing 114 such as the StatLock® IV stabilization device manufactured for Becton-Dickinson Nexiva™ catheters 112. In any case, the dressing 114 may receive the catheter adapter 102 and retain the catheter adapter 102 in a substantially stable position relative to the dressing 114.

In some embodiments, the incline device 900 may be coupled to a proximal side or end 118 of the stabilizer element 700. Some embodiments of the incline device 900 may include one or more snap arms 906 to pivot from an attachment point 908. In operation, some embodiments of the incline device 900 may pivot forward in a distal direction and may snap into place such that the distal end 106 of the catheter adapter 102 is pivoted closer to an insertion site of the catheter 112. This may reduce a risk of the catheter 112 kinking at the distal end 106 of the catheter adapter 102 while moving the tip 120 of the catheter 112 forward within the vasculature to improve access to blood.

In other embodiments, the snap arms 906 may pivot in a proximal direction such that the snap arms 906 snap into place at the proximal side or end of the dressing 114. This may pivot the catheter adapter 102 backwards, lifting the distal end 106 of the catheter adapter 102 and moving the tip 120 of the catheter 112 in a proximal direction within the vasculature. In still other embodiments, the incline device 900 may rotate back and clip onto the proximal end 104 of the catheter adapter 102. In any case, in some embodiments the incline device 900 may reposition the angle of the catheter adapter 102 and thereby reposition the tip 120 of the catheter 112 within the vasculature.

Figure 10A:
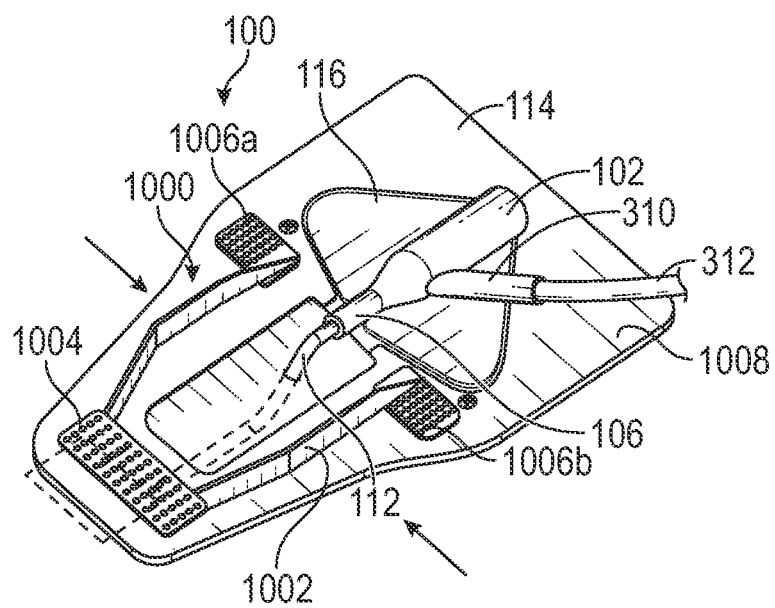
FIG. 10A is a perspective view of another example catheter assembly and another example dressing to apply traction to the catheter according to some embodiments.
Figure 10B:
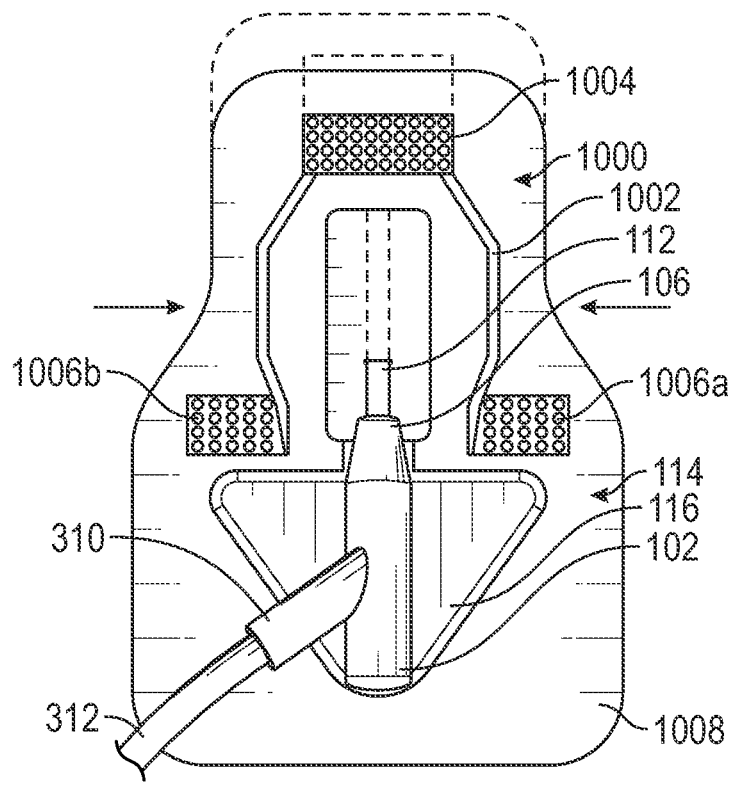
FIG. 10B is an upper perspective view of the catheter assembly and dressing of FIG. 10A.

Referring now to FIGS. 10A and 10B, in some embodiments, the catheter assembly 100 may include the dressing 114 to receive the catheter adapter 102 and a traction mechanism 1000 coupled to the dressing 114 to consistently apply traction to the catheter 112 extending from the catheter adapter 102. As shown in FIG. 10A, in some embodiments, the dressing 114 may include a stabilization pad 1008 having a contour to receive and stabilize the catheter adapter 102 and/or the stabilizer element 700 coupled thereto.

Some embodiments of the traction mechanism 1000 may be coupled to the stabilization pad 1008 at a location substantially corresponding to a position of the catheter 112. In some embodiments, the traction mechanism 1000 may include anchor points 1006 located on either side of the catheter 112 at or near its proximal end. In some embodiments, traction arms 1002 may extend distally from the anchor points 1006 parallel to the catheter 112. In some embodiments, a traction plate 1004 extending in a substantially transverse direction relative to the traction arms 1002 may be coupled to or integrated with the distal ends of the traction arms 1002. In some embodiments, the traction plate 1004 may provide a distal anchor point for the traction mechanism 1000.

In operation, in some embodiments, the traction arms 1002 may be squeezed inwardly to straighten or to deform a contour of each of the traction arms 1002 in an inward direction relative to the catheter 112. In some embodiments, this application of force may apply controlled traction to the catheter 112 to open a fluid path within the vasculature.

Figure 11:
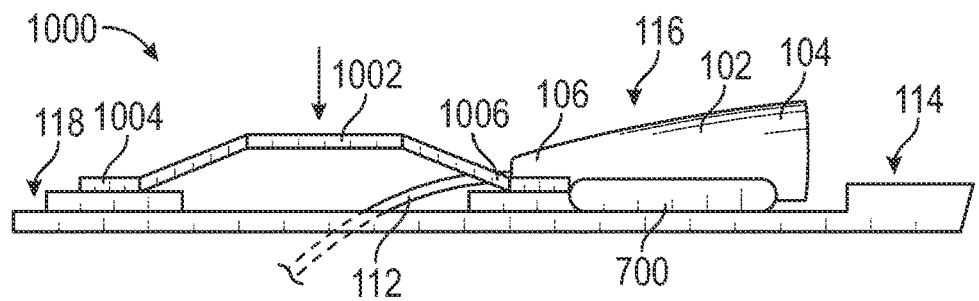
FIG. 11 is a side view of an example catheter assembly and an example dressing according to some embodiments.

Referring now to FIG. 11, in alternative embodiments, the traction mechanism 1000 may include one or more traction arms 1002 configured to be pressed down or displaced in a downward direction relative to the catheter 112. In some embodiments, this downwardly applied force may extend the traction mechanism 1000 and thereby lengthen a distance between the anchor points 1006 located adjacent to a proximal end of the catheter 112 and the traction plate 1004 located adjacent to the tip 120 of the catheter 112. In this manner, the traction mechanism 1000 may be actuated to consistently apply traction to the catheter 112.

Figure 12:
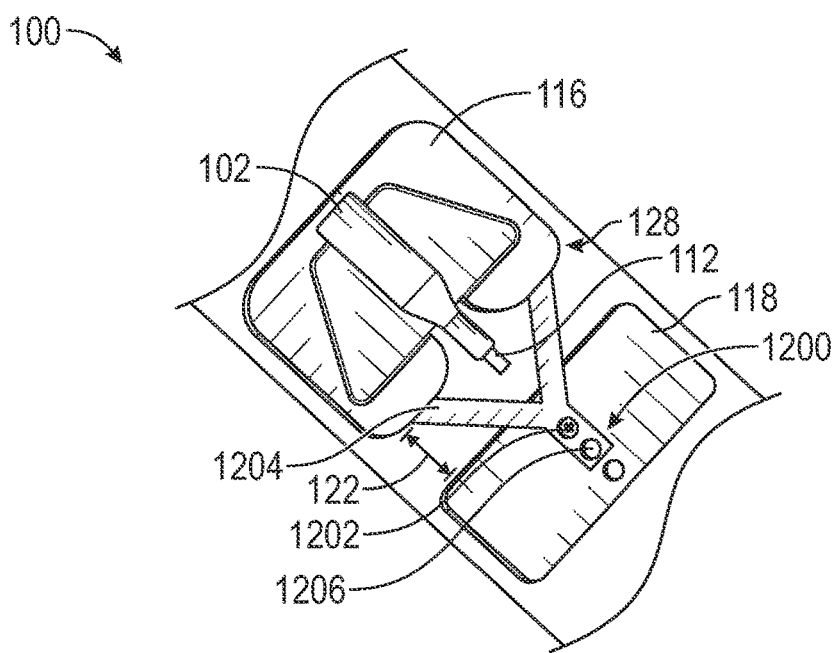
FIG. 12 is an upper perspective view of another example catheter assembly and another example dressing to apply traction to the catheter according to some embodiments.
Figure 13:
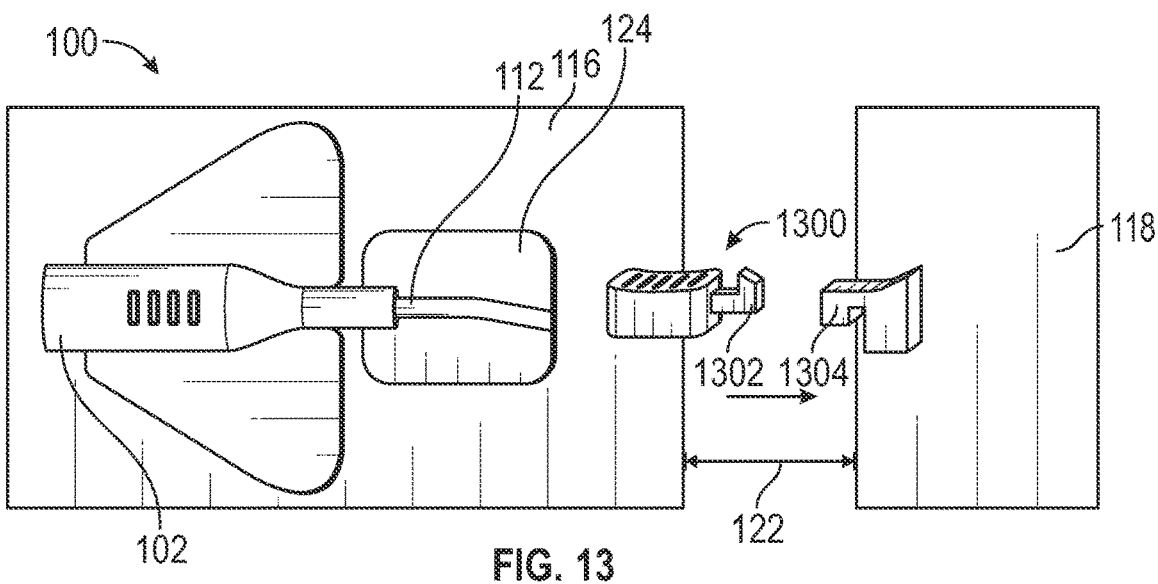
FIG. 13 is an upper perspective view of another example catheter assembly and another example dressing according to some embodiments.

Referring now to FIGS. 12 and 13, in some embodiments, the first section 116 of the dressing 114 may include a contour, adhesive and/or other feature to retain the catheter adapter 102 in a substantially fixed position relative to the patient. The second section 118 of the dressing 114 may be spaced apart from the first section 116 and may be substantially fixed relative to the patient via an adhesive or other suitable device or mechanism. In this manner, in some embodiments, a substantially constant distance 122 may separate the first section 116 and the second section 118.

In some embodiments, the traction mechanism 1000 may be coupled to the first section 116 of the dressing 114 and may be configured to attach to the second section 118 of the dressing 114 to adjust the distance between the same. In some embodiments, the traction mechanism 1000 may include an adjustable snap feature 1200 to adjust the distance between the first section 116 and the second section 118. In this manner, some embodiments of the snap feature 1200 may apply consistent traction to the catheter 112.

As shown in FIG. 12, in some embodiments, the traction mechanism 1000 may include a tension strap 1204 coupled to the first section 116 of the dressing 114. In some embodiments, the tension strap 1204 may be monolithically formed as a single unit with the first section 116 of the dressing 114. In some embodiments, the catheter adapter 102 and/or stabilizer element 700 may be coupled to the tension strap 1204. In other embodiments, the tension strap 1204 may substantially surround the catheter adapter 102 and/or stabilizer element 700.

In any case, some embodiments of the tension strap 1204 may include the snap feature 1200 coupled to or integrated with its distal end. In some embodiments, the snap feature 1200 may include an extension or tab having one or more snap caps 1206 disposed along a length thereof. In some embodiments, each snap cap 1206 may be configured to couple to a socket 1202 coupled to or integrated with the second section 118 of the dressing 114. In some embodiments, the second section 118 may include multiple sockets 1202 such that one or more of the snap caps 1206 may be adjustably coupled to one or more of the sockets 1202. In this manner, in some embodiments, the tension strap 1204 may be tightened and/or loosened relative to the second section 118 of the dressing 114 to adjust traction applied to the catheter 112 in a controlled manner.

Referring now to FIG. 13, in some embodiments, the tension strap 1204 or dressing 114 may include an alternative connection feature 1300 such as a clasp, buttons, hook and loop fasteners such as Velcro®, adhesive, or other suitable securement device or feature. As shown, in some embodiments, the connection feature 1300 may include a first connector element 1302 coupled to the first section 116 of the dressing 114 and a second connector element 1304 coupled to the second section 118 of the dressing 114. In some embodiments, the first connector element 1302 and/or the second connector element 1304 may be adjustable to adjust the distance 122 between the first section 116 of the dressing 114 and the second section 118 of the dressing 114. In some embodiments, the first connector element 1302 and the second connector element 1304 may interlock or may be otherwise coupled together to reduce the distance 122 between the first section 116 and the second section 118 to thereby apply traction to the catheter 112 in a consistent manner.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:
   a catheter adapter comprising a proximal end, a distal end, and a longitudinal axis extending between the proximal end and the distal end;
   a catheter extending from the distal end of the catheter adapter;
   a dressing to apply traction to the catheter in response to the catheter being disposed within a vasculature of a patient, the dressing comprising a first section adjustably coupled to a second section, wherein the first section is configured to secure at least one of the catheter adapter and the catheter to the patient, wherein the first section includes an aperture configured to surround an insertion site of the catheter, and wherein the second section is distal to the first section and positionable on a side of the aperture opposite the proximal end of the catheter adapter, the second section configured to be adjustably secured relative to the first section along the longitudinal axis of the catheter adapter to apply the traction to the catheter within the vasculature; and
   an adjustment element to adjustably couple the first section to the second section, wherein the adjustment element comprises a plurality of tethers coupled to and extending between the first section and the second section, and wherein each of the plurality of tethers is configured to be adjusted individually to apply the traction on the catheter.

2. The catheter assembly of claim 1, wherein the first section and the second section are positionable independent of each other.

3. The catheter assembly of claim 1, wherein the aperture is configured to receive at least a portion of the catheter adapter or at least a portion of the catheter.

4. The catheter assembly of claim 1, wherein the first section comprises an adhesive to secure the at least one of the catheter adapter and the catheter relative to the patient.

5. The catheter assembly of claim 1, wherein the second section is configured to be secured directly to the patient.

6. The catheter assembly of claim 1, wherein the adjustment element is releasable to decouple the first section and the second section.

7. The catheter assembly of claim 1, wherein the second section is configured to be spaced apart from the first section along the longitudinal axis of the catheter adapter.

8. The catheter assembly of claim 1, wherein the second section is distal to the catheter adapter.

9. A catheter assembly, comprising:
   a catheter adapter comprising a proximal end, a distal end, and a longitudinal axis extending between the proximal end and the distal end;
   a catheter extending from the distal end of the catheter adapter;
   a dressing to apply traction to the catheter in response to the catheter being disposed within a vasculature of a patient, the dressing comprising a first section adjustably coupled to a second section, wherein the first section is configured to secure at least one of the catheter adapter and the catheter to the patient, wherein the first section includes an aperture configured to surround an insertion site of the catheter, and wherein the second section is distal to the first section and positionable on a side of the aperture opposite the proximal end of the catheter adapter, the second section configured to be adjustably secured relative to the first section along the longitudinal axis of the catheter adapter to apply the traction to the catheter within the vasculature; and an adjustment element to adjustably couple the first section to the second section, wherein the adjustment element comprises a plurality of tethers coupled to and extending between the first section and the second section, and wherein the plurality of tethers is configured to be adjusted collectively to apply the traction on the catheter.

10. The catheter assembly of claim 9, wherein the first section and the second section are positionable independent of each other.

11. The catheter assembly of claim 9, wherein the aperture is configured to receive at least a portion of the catheter adapter or at least a portion of the catheter.

12. The catheter assembly of claim 9, wherein the first section comprises an adhesive to secure the at least one of the catheter adapter and the catheter relative to the patient.

13. The catheter assembly of claim 9, wherein the second section is configured to be secured directly to the patient.

14. The catheter assembly of claim 9, wherein the adjustment element is releasable to decouple the first section and the second section.

15. The catheter assembly of claim 9, wherein the second section is configured to be spaced apart from the first section along the longitudinal axis of the catheter adapter.

16. The catheter assembly of claim 9, wherein the second section is distal to the catheter adapter.

\* \* \* \* \*